United States Patent
Al-Hazmi et al.

(10) Patent No.: US 10,421,064 B2
(45) Date of Patent: Sep. 24, 2019

(54) CATALYST COMPOSITION AND PROCESS FOR OLIGOMERIZATION OF ETHYLENE TO PRODUCE 1-HEXENE AND/OR 1-OCTENE

(71) Applicant: SABIC GLOBAL TECHNOLOGIES B.V., Bergen Op Zoom (NL)

(72) Inventors: Mohammed H. Al-Hazmi, Riyadh (SA); Abdullah Alqahtani, Riyadh (SA); Uwe Rosenthal, Lambrechtshagen (DE); Bernd H. Muller, Rostock (DE); Normen Peulecke, Rostock (DE); Marco Harff, Munich (DE); Anina Wohl, Pullach (DE); Andreas Meiswinkel, Munich (DE); Heinz Bolt, Wolfratshausen (DE); Wolfgang Muller, Munich (DE)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 15/326,781

(22) PCT Filed: Jul. 22, 2015

(86) PCT No.: PCT/IB2015/055532
§ 371 (c)(1),
(2) Date: Jan. 17, 2017

(87) PCT Pub. No.: WO2016/012948
PCT Pub. Date: Jan. 28, 2016

(65) Prior Publication Data
US 2017/0203288 A1 Jul. 20, 2017

Related U.S. Application Data

(60) Provisional application No. 62/028,558, filed on Jul. 24, 2014.

(51) Int. Cl.
*B01J 31/18* (2006.01)
*B01J 31/14* (2006.01)
*C07C 2/32* (2006.01)

(52) U.S. Cl.
CPC ........... *B01J 31/187* (2013.01); *B01J 31/143* (2013.01); *C07C 2/32* (2013.01); *B01J 2231/20* (2013.01); *B01J 2531/62* (2013.01); *C07C 2531/14* (2013.01); *C07C 2531/18* (2013.01)

(58) Field of Classification Search
None
See application file for complete search history.

(56) References Cited

U.S. PATENT DOCUMENTS

| | | | |
|---|---|---|---|
| 6,800,702 B2 | 10/2004 | Wass | |
| 7,361,623 B2 | 4/2008 | Dixon et al. | |
| 2008/0242811 A1 | 10/2008 | Gao et al. | |
| 2010/0190939 A1 | 7/2010 | Fritz et al. | |
| 2010/0240847 A1* | 9/2010 | Dixon | B01J 31/188 526/161 |

FOREIGN PATENT DOCUMENTS

| | | | |
|---|---|---|---|
| CN | 101646684 A | 2/2010 | |
| TW | 200942327 A | 10/2009 | |
| WO | 2004056479 A1 | 7/2004 | |
| WO | 2008077908 A1 | 7/2008 | |
| WO | 2009006979 A2 | 1/2009 | |
| WO | WO-2009006979 A2 * | 1/2009 | ............ B01J 31/143 |
| WO | 2009068157 A1 | 6/2009 | |
| WO | 2010115520 A1 | 10/2010 | |
| WO | 2012045147 A1 | 4/2012 | |
| WO | 2013137676 A1 | 9/2013 | |

OTHER PUBLICATIONS

Hill et al. (Inorg. Chem., 1989, 28, 3461-3467). (Year: 1989).*
Taiwanese Office Action for application No. 104123898 dated Jun. 6, 2017, 5 pages.
Albahily et al., "Vinyl Oxidative Coupling as a Synthetic Route to Catalytically Active Monovalent Chromium." J. Am.Chem.Soc., 2011, 133 (16), pp. 6388-6395.
International Search Report and Written Opinion for International Application No. PCT/IB2015/055532; International Filing Date—Jul. 22, 2015; dated Nov. 30, 2015.
Product Data Sheet, "MMAO-3A/Toluene Solutions (Modified Methylaluminoxane, type 3A)" Metal Alkyls, MA 66719.02; Dec. 2003; 2 pages.
Yang et al., "Selective Ethylene Tri-/Tetramerization by in Situ-Formed Chromium Catalysts Stabilized by N,P-Based Ancillary Ligand Systems"; ACS Catalysis, pp. 2353 2361; Published Sep. 3, 2013, 9 pages.
International Preliminary Report on Patentability; International Application No. PCT/IB2015/055532; International Filing Date—Jul. 22, 2015; dated Jan. 24, 2017; 6 pages.

* cited by examiner

*Primary Examiner* — Yun Qian
(74) *Attorney, Agent, or Firm* — Cantor Colburn LLP

(57) ABSTRACT

The present invention relates to a catalyst composition and a process for the oligomerization of ethylene to produce 1-hexene or 1-octene, wherein the catalyst composition comprises a chromium compound; an NPNPN ligand of the formula $(R^1)\ (R^2)N-P(R^3)-N(R^4)-P(R^5)-N(R^6)(R^7)$, wherein $R^1$, $R^2$, $R^3$, $R^4$, $R^5$, $R^6$ and $R^7$ are each independently hydrogen, halogen, amino, trimethylsilyl or $C_1$-$C_{20}$ hydrocarbyl, preferably straight-chain or branched $C_1$-$C_{10}$ alkyl, phenyl, $C_6$-$C_{20}$ aryl or $C_6$-$C_{20}$ alkyl-substituted phenyl.

20 Claims, No Drawings

CATALYST COMPOSITION AND PROCESS FOR OLIGOMERIZATION OF ETHYLENE TO PRODUCE 1-HEXENE AND/OR 1-OCTENE

This application is a National Stage application of International Application No. PCT/IB2015/055532, filed Jul. 22, 2015, which claims the benefit of U.S. Provisional Application No. 62/028,558, filed Jul. 24, 2014, both of which are incorporated by reference in their entirety herein.

BACKGROUND

Existing processes for the production of linear alpha olefins (LAOs), including comonomer-grade 1-butene, 1-hexene, and 1-octene, rely on the oligomerization of ethylene, and lead to a mixture of ethylene oligomers having a chain length of 4, 6, 8, and so on. Without being bound by specific theory, this is due to a chemical mechanism mainly governed by competing chain growth and displacement reaction steps, leading to a Schulz-Flory- or Poisson-product distribution. From a commercial standpoint this product distribution poses a formidable challenge for the full-range linear alpha olefins producer. The reason is that each served market segment exhibits a very different behavior in terms of market size and growth, geography, fragmentation etc. It is, therefore, very difficult for the LAO producer to adapt to the market requirements since part of the product spectrum might be in high demand in a given economic context, while at the same time other product fractions might not be marketable at all or only in a marginal niche.

LAOs such as 1-butene, 1-hexene, and 1-octene are suitable for the production of polyethylene, including linear low density polyethylene (LLDPE). Currently, the main LAO used in the production of polyethylene is 1-butene, followed by 1-hexene. Demand for the latter has increased, which can be attributed to the superior properties of polyethylene made from 1-hexene. At the same time, certain grades of polyethylene materials call for improved physical properties such as superior tensile strength and crack resistance, requiring the presence of 1-octene.

Oligomerization of ethylene usually proceeds in the presence of suitable catalysts. Several of the existing ethylene oligomerization, i.e., dimerization, trimerization or tetramerization, catalysts have one or more disadvantages. These shortcomings, which can affect the corresponding processes wherein these catalysts are used, include one or more of low selectivity for the desirable products, i.e., 1-hexene or 1-octene (due to formation of undesired byproducts from side reactions); low purity of the products themselves, i.e., low selectivities for the LAO isomer within a specific C6- or C8-cut (isomerization, branched olefin formation etc.); wax formation, i.e., formation of heavy, long-chain (high carbon-number) products; polymer formation (polyethylene, including branched and/or cross-linked PE), which this may lead to considerable LAO product yield loss as well as fouling of equipment; poor turnover rates/catalyst activity, resulting in increased cost per kg product; high catalyst- or ligand cost; complex, multi-step ligand synthesis, resulting in poor catalyst availability and high catalyst cost; susceptibility of catalyst performance, both in terms of both activity and selectivity, to trace impurities (leading to, for example, catalyst losses/poisoning); difficult handling of catalyst components in a technical/commercial environment (e.g., during catalyst complex synthesis, pre-mixing, inertization, catalyst recovery, or ligand recovery); harsh reaction conditions, i.e., high temperatures and pressure, resulting in a need for special equipment (increased investment-, maintenance-, and energy costs); high co-catalyst/activator cost or consumption; susceptibility to varying co-catalyst qualities, which is often the case when larger amounts of relatively ill-defined compounds are used as activators (e.g., certain MAO-varieties).

There accordingly remains a need in the art for catalyst systems for the oligomerization of ethylene that can yield 1-octene or 1-hexene with high selectivity. There remains a further need in the art for catalyst systems that can furnish combinations of 1-octene and 1-hexene. At the same time, there remains a need in the art for catalyst systems that can provide combinations of 1-octene and 1-hexene at a predetermined ratio, wherein the predetermined ratio has been a range of available ratios that the catalyst system also provides. There also remains a need for processes for the oligomerization of ethylene to produce 1-octene and 1-hexene in high purity and at variable ratios.

SUMMARY

Disclosed herein are catalyst compositions for the oligomerization of ethylene to produce 1-hexene or 1-octene, the catalyst composition comprising:
a chromium compound;
an NPNPN ligand of the formula

wherein $R^1$, $R^2$, $R^3$, $R^4$, $R^5$, $R^6$, and $R^7$ are each independently hydrogen, halogen, amino, trimethylsilyl or $C_1$-$C_{20}$ hydrocarbyl, preferably straight-chain or branched $C_1$-$C_{10}$ alkyl, phenyl, $C_6$-$C_{20}$ aryl or $C_6$-$C_{20}$ alkyl-substituted phenyl, optionally wherein the ligand is a cyclic derivative wherein at least one of the P or N atoms of the ligand is a member of a ring system, or any cyclic derivative thereof wherein at least one of the P or N atoms of the NPNPN ligand is a member of a ring system, the ring system being formed from one or more constituent compounds of the ligand by substitution; and
an activator or co-catalyst.

Also disclosed herein are processes for the oligomerization of ethylene, comprising contacting ethylene with the above-described catalyst compositions under ethylene oligomerization conditions effective to produce 1-hexene or 1-octene.

Further disclosed herein are catalyst compositions obtained by combining at least:
a chromium compound;
an NPNPN ligand of the formula

wherein $R^1$, $R^2$, $R^3$, $R^4$, $R^5$, $R^6$, and $R^7$ are each independently hydrogen, halogen, amino, trimethylsilyl or $C_1$-$C_{20}$ hydrocarbyl, preferably straight-chain or branched $C_1$-$C_{10}$ alkyl, phenyl, $C_6$-$C_{20}$ aryl or $C_6$-$C_{20}$ alkyl-substituted phenyl, optionally wherein the ligand is a cyclic derivative wherein at least one of the P or N atoms of the ligand is a member of a ring system, or any cyclic derivative thereof wherein at least one of the P or N atoms of the NPNPN ligand is a member of a ring system, the ring system being formed from one or more constituent compounds of the ligand by substitution; and
an activator or co-catalyst.

Additionally disclosed herein is an ethylene oligomerization reaction producing 1-hexene and 1-octene, wherein the selectivity for 1-hexene or 1-octene is at least about 90%.

Also disclosed herein is a linear alpha olefin composition resulting from an ethylene oligomerization process, wherein a ratio by weight of 1-hexene to 1-octene is at least about 0.2 to about 8.

DETAILED DESCRIPTION

The inventors hereof have discovered catalyst compositions for the oligomerization of ethylene to produce 1-hexene or 1-octene, that is, hexene, 1-octene, or a combination comprising at least one or both of the foregoing. The catalyst compositions include (i) a chromium compound; (ii) an NPNPN ligand of the formula $(R^1)(R^2)N$—$P(R^3)$—$N(R^4)$—$P(R^5)$—$N(R^6)(R^7)$ and (iii) an activator or co-catalyst. The catalyst compositions are useful in a process for the oligomerization of ethylene to produce 1-hexene or 1-octene. The inventors hereof have further discovered that when the catalyst compositions are used in the process, the 1-hexene or 1-octene can be produced with superior selectivity, productivity, and purity. Furthermore, combinations comprising 1-hexene and 1-octene can be produced wherein a ratio by weight of 1-hexene to 1-octene can be predetermined in the range from about 0.1 to about 10, preferably from about 0.2 to about 8, more preferably from about 0.3 to about 7.

The chromium compound is an organic salt, an inorganic salt, a coordination complex, or an organometallic complex of Cr(II) or Cr(III). In an embodiment, the chromium compound is an organometallic complex, preferably of Cr(II) or Cr(III). Examples of the chromium compounds include Cr(III)acetylacetonate, Cr(III)octanoate, $CrCl_3$(tetrahydrofuran)$_3$, Cr(III)-2-ethylhexanoate, chromium hexacarbonyl, Cr(III)chloride, benzene(tricarbonyl)-chromium. A combination comprising at least one of the foregoing chromium compounds can be used.

In the NPNPN ligand, $R^1$, $R^2$, $R^3$, $R^4$, $R^5$, $R^6$, and $R^7$ can be each independently hydrogen, halogen, amino, trimethylsilyl, or $C_1$-$C_{20}$ hydrocarbyl. Preferably the $C_1$-$C_{20}$ hydrocarbyl is straight-chain or branched $C_1$-$C_{10}$ alkyl, phenyl, $C_6$-$C_{20}$ aryl or $C_6$-$C_{20}$ alkyl-substituted phenyl. More preferably, each $R^1$, $R^2$, $R^3$, $R^4$, $R^5$, $R^6$, and $R^7$ is independently hydrogen (H), chloro (Cl), methyl (Me), ethyl (Et), isopropyl ($^i$Pr), tert-butyl ($^t$Bu), n-hexyl ($C_6H_{11}$), or phenyl (Ph).

Optionally, the ligand can be a cyclic derivative wherein at least one of the P or N atoms of the ligand is a member of a ring system, or any cyclic derivative thereof wherein at least one of the P or N atoms of the NPNPN ligand is a member of a ring system. The ring system can be formed from one or more constituent compounds of the NPNPN ligand by substitution, i.e., by formally eliminating per constituent compound either two whole groups $R_1$-$R_7$ (as defined), one atom from each of two groups $R_1$-$R_7$ (as defined) or a whole group $R_1$-$R_7$ (as defined) and an atom from another group $R_1$-$R_7$ (as defined), and joining the formally so-created valence-unsaturated sites by one covalent bond per constituent compound to provide the same valence as initially present at a given site.

Specific suitable NPNPN ligands are Et(Me)N—P(Ph)-N(Me)-P(Ph)-N(Me)Et, $C_6H_{11}$(Me)N—P(Ph)-N(Me)-P(Ph)-N(Me)$C_6H_{11}$, $^i$Pr(Me)N—P(Ph)-N(Me)-P(Ph)-N(Me)$^i$Pr, H($^t$Bu)N—P(Ph)-N(Me)-P(Ph)-N($^t$Bu)H, $(C_6H_{11})_2$N—P(Ph)-N(Me)-P(Ph)-N$(C_6H_{11})_2$, $^i$Pr(Ph)N—P(Ph)-N(Me)-P(Ph)-N(Ph)$^i$Pr, H(Ph)N—P(Ph)-N(Me)-P(Ph)-N(Ph)H, H($^i$Pr)N—P(Ph)-N($^i$Pr)—P(Ph)-N($^i$Pr)H, Et(Me)N—P(Ph)-N$(C_6H_{11})$—P(Ph)-N(Me)Et, and Et(Me)N—P(Me)-N(Me)-P(Me)-N(Me)Et. A combination comprising at least one of the foregoing NPNPN ligands can be used.

The structure of the NPNPN ligand can also be illustrated by the following structural formula (A):

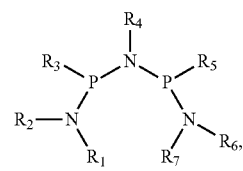

(A)

wherein $R^1$, $R^2$, $R^3$, $R^4$, $R^5$, $R^6$, and $R^7$ are defined as above.

The structures of specific examples of the NPNPN ligand are shown in the following structural formulae (A1) to (A10).

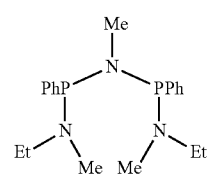

(A1)

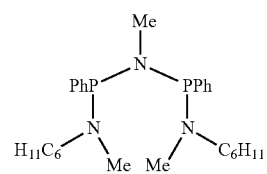

(A2)

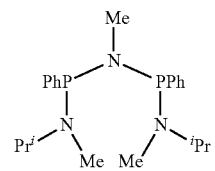

(A3)

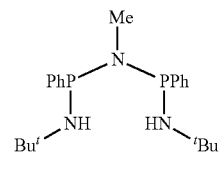

(A4)

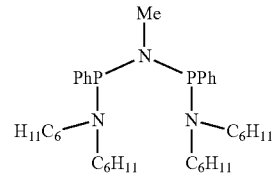

(A5)

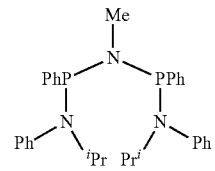

(A6)

-continued

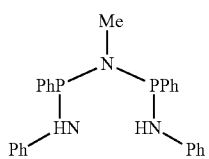
(A7)

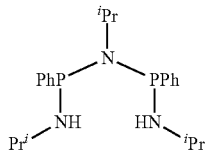
(A8)

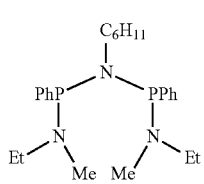
(A9)

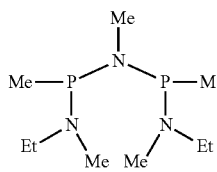
(A10)

A combination comprising at least one of the formulae (A1) to (A10) can be used.

The NPNPN ligand can be made by synthetic approaches known to those skilled in the art. In some embodiments, a $(R^1)(R^2)N$—$P(R^3)$—$N(R^4)$—$P(R^5)$—$N(R^6)(R^7)$ ligand is accessible by reaction pathways as shown in Scheme 1.

Scheme 1

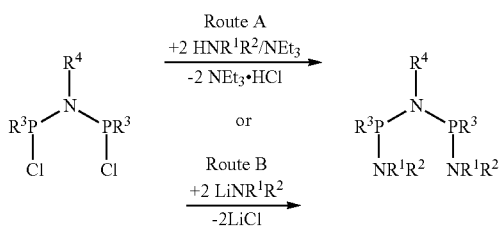

In Scheme I, $R^1$ to $R^4$ have the meanings as described above.

The activator (also known in the art as a co-catalyst) is an aluminum compound, for example trimethylaluminum, triethylaluminum, triisopropylaluminum, triisobutylaluminum, diethylaluminum chloride, ethylaluminum sesquichloride, ethylaluminum dichloride, methylaluminoxane. A combination of different aluminum compounds can be used. A combination comprising at least one of the foregoing aluminum compounds can be used. In some embodiments the activator is preferably a modified methylaluminoxane, more preferably MMAO-3A(CAS No. 146905-79-5), which is a modified methylaluminoxane, type 3A, available from Akzo Nobel in toluene solution containing 7% aluminum, which corresponds to an MMAO-3A concentration of about 18%.

The catalyst composition can further contain a solvent. Exemplary solvents are aromatic hydrocarbons, straight-chain and cyclic aliphatic hydrocarbons, straight-chain olefins, ethers, and the like. A combination comprising at least one of the foregoing solvents can be used. Preferably, the solvent is toluene, chlorobenzene, o-dichlorobenzene, bromobenzene, chlorocyclohexane, chlorohexane, multiple halogenated aromatic mixtures, or a combination comprising at least one of the foregoing. Toluene solvent is more preferred.

The concentration of the chromium compound can vary depending on the particular compound used and the desired reaction rate. In some embodiments the concentration of the chromium compound is from about 0.01 to about 100 millimole per liter (mmol/l), about 0.01 to about 10 mmol/l, about 0.01 to about 1 mmol/l, about 0.1 to about 100 mmol/l, about 0.1 to about 10 mmol/l, about 0.1 to about 1.0 mmol/l, about 1 to about 10 mmol/l, and about 1 to about 100 mmol/l. Preferably, the concentration of the chromium compound is from about 0.1 to about 1.0 mmol/l.

The molar ligand/Cr ratio can be from about 0.5 to 50, about 0.5 to 5, about 0.8 to about 2.0, about 1.0 to 5.0, or preferably from about 1.0 to about 1.5.

The molar Al/Cr ratio can be from about 1 to about 1000, about 10 to about 1000, about 1 to 500, about 10 to 500, about 10 to about 300, about 20 to about 300, or preferably from 50 to about 300.

In some embodiments, the catalyst composition includes Cr(III)acetylacetonate as the chromium compound; Et(Me)N—P(Ph)-N(Me)-P(Ph)-N(Me)Et as the NPNPN ligand; and MMAO-3A as the activator.

The catalyst composition disclosed herein can be used in a process for the oligomerization of ethylene. In an embodiment, the process encompasses contacting ethylene with the catalyst composition under ethylene oligomerization conditions effective to produce 1-hexene or 1-octene. Those skilled in the art will understand that oligomerization of ethylene to produce 1-hexene can be by trimerization of ethylene, and oligomerization of ethylene to produce 1-octene can be by tetramerization of ethylene.

The oligomerization of ethylene can be carried out at a pressure of from about 1 to about 200 bar, about 10 to about 200 bar, about 10 to about 100 bar, about 20 to about 70 bar, and about 10 to 50 bar. Preferably, the oligomerization is at a pressure from about 20 to about 70 bar.

The oligomerization of ethylene can also be performed at a temperature of from about 10 to about 200° C., about 20 to about 100° C., about 30 to about 100° C., about 40 to about 100° C., about 40 to about 80° C., preferably about 40 to about 70° C.

In another embodiment, the process is carried out continuously, semi-continuously or discontinuously.

The process is usually carried out in a suitable reactor. The time it takes for the process to be carried out, usually in the reactor, is also known as residence time. The mean residence time of the process may be from about 10 minutes to about 20 hours, about 20 minutes to about 20 hours, about 1 hour to about 16 hours, about 1 hour to about 8 hours, preferably about 1 to about 4 hours.

As those skilled in the art can understand, the chromium compound, NPNPN ligand, and activator, necessary as components for the catalyst composition, can also be regarded as starting materials. As such, without being bound by specific theory, these three components can undergo transformation or conversion when brought into contact, for example by mixing, whereby the catalyst composition is usually formed. It is thus an advantageous feature that the catalyst can be obtained by combining at least: the chromium compound; the NPNPN ligand of the formula $(R^1)(R^2)N$—$P(R^3)$—N ($R^4$)—P($R^5$)—N($R^6$)($R^7$), wherein $R_1$, $R_2$, $R_3$, $R_4$, $R_5$, $R_6$ and $R_7$ are defined as above; and the activator or co-catalyst.

Surprisingly, it was found that with the catalyst composition and process for the oligomerization of ethylene to produce 1-hexene or 1-octene, that the disadvantages of existing catalysts and processes can be significantly overcome. Especially surprising and unexpected was the finding that the ratio by weight of 1-hexene and 1-octene can be varied to a considerable extent. Without being bound by specific theory, it is believed that this variation can be governed by advantageously selecting $R^1$, $R^2$, $R^3$, $R^4$, $R^5$, $R^6$, and $R^7$ in the NPNPN ligand. In an embodiment, the weight ratio of 1-hexene to 1-octene is in the range from about 0.1 to about 10, preferably from about 0.2 to about 8, more preferably from about 0.3 to about 7. The weight ratio of 1-hexene to 1-octene can be in the range from about 0.1 to about 9, about 0.1 to about 8, about 0.1 to about 7, about 0.1 to about 6, about 0.2 to about 10, about 0.2 to about 9, about 0.2 to about 7, about 0.2 to about 6, about 0.3 to about 10, about 0.3 to about 9, about 0.3 to about 8, or about 0.3 to about 6. The 1-hexene to 1-octene ratio by weight can also be at least about 0.1, about 0.2, about 0.3, about 0.4, about 0.5, about 0.6, about 0.7, about 0.8, about 0.9, or about 1. The weight ratio of 1-hexene to 1-octene can be up to about 10, about 9, about 8, about 7, about 6, about 5, about 4, about 3, about 2, about 1.5, or about 1.2.

As discussed above, the process and catalyst composition disclosed herein allow for the production of $C_6$ and $C_8$ fractions with high selectivity. Furthermore, within the $C_6$ or $C_8$ fraction, selectivity for the corresponding LAO is increased. Thereby, no wide LAO product distribution is observed, and specific linear alpha-olefins, i.e., 1-hexene or 1-octene, can be selectively produced. High selectivity for 1-hexene or 1-octene is an advantageous feature inasmuch as it leads to higher product purity, thereby circumventing the need for additional purification steps in the separation train. Further advantageous features of the catalyst composition and process include suppression of ethylene polymerization leading to undesirable polymer formation, milder reaction conditions and, as a result, lower capital costs for equipment as well as operational and energy costs. Additionally, a relatively simple, straight-forward process design is possible.

In another embodiment, selectivity for 1-hexene or 1-octene can be at least about 75%, about 80%, about 85%, about 90%, about 95%, about 96%, about 97%, about 98%, or about 99%. A selectivity of at least about 90% is preferred.

In order that the invention disclosed herein may be more efficiently understood, the following examples are provided. These examples are for illustrative purposes only and are not to be construed as limiting the invention in any manner

EXAMPLES

Example 1

Preparation of Ligands (A1)-(A10)

1.1 Route A, General Procedure (cf. Scheme 1)

3 mmol of the bis(chlorophosphino)amine RP(Cl)N(R')P(Cl)R, dissolved in toluene, was slowly transferred into a mixture of 8 mmol of appropriate secondary or primary amine, 6 mmol $NEt_3$ and toluene at about 0° C. The solution was stirred for 24 hrs. at 40° C. whereupon it became cloudy. After evaporation of all volatile compounds, the residue was taken up in hot n-hexane and filtrated. Evaporation of the solvent led to colorless oils or solids. If desired, the products can be recrystallized from ethanol or n-pentane to increase the purity.

1.2 Route B, General Procedure (cf. Scheme 1)

6 mmol of the appropriate secondary amine was lithiated with an equivalent amount of MeLi in $Et_2O$ at about 0° C. The solution was then stirred for 6 hrs at room temperature, cooled again to about 0° C. and treated with an etheric solution of 3 mmol of the bis(chlorophosphino) amine RP(Cl)N(R)P(Cl)R, and additionally stirred for 24 hrs at room temperature. Workup is equivalent to Route A.

Precursor PhP(Cl)N(Me)P(Cl)Ph was prepared by modifying the procedure of R. Jefferson, J. F. Nixon, T. M. Painter, R. Keat, L. Stobbs *J. Chem. Soc. Dalton Trans.* 1973, 1414-1419.

The same procedure was used for PhP(Cl)N($C_6H_{11}$)P(Cl)Ph ($Me_3SiN(C_6H_{11})SiMe_3$ instead of $Me_3SiN(Me)SiMe_3$), for PhP(Cl)N($^iPr$)P(Cl)Ph ($Me_3SiN(^iPr)SiMe_3$ instead of $Me_3SiN(Me)SiMe_3$) and for MeP(Cl)N(Me)P(Cl)Me ($MePCl_2$ instead of $PhPCl_2$).

Preparation of $Me_3SiN(^iPr)SiMe_3$ and $Me_3SiN(C_6H_{11})SiMe_3$ was performed according to Y. Hamada, Y. Yamamoto, H. Shimizu *J. Organomet. Chem.* 1996, 510, 1-6.

Thus Ligands (A1) to (A10) were prepared. These were characterized as follows:

Et(Me)N—P(Ph)-N(Me)-P(Ph)-N(Me)Et (A1), Route A, $^{31}$P-NMR $C_6D_6$: 101.6; 101.9 ppm, isomers;

$C_6H_{11}$(Me)N—P(Ph)-N(Me)-P(Ph)-N(Me)$C_6H_{11}$ (A2), Route B, $^{31}$P-NMR $C_6D_6$: 98.2; 99.6 ppm, isomers;

$^iPr$(Me)N—P(Ph)-N(Me)-P(Ph)-N(Me)$^iPr$ (A3), Route A, $^{31}$P-NMR $C_6D_6$: 99.5; 100.3 ppm, isomers;

H($^tBu$)N—P(Ph)-N(Me)-P(Ph)-N($^tBu$)H (A4), Route A, $^{31}$P-NMR $C_6D_6$: 64.6 ppm, major isomer isolated;

$(C_6H_{11})_2$N—P(Ph)-N(Me)-P(Ph)-N$(C_6H_{11})_2$ (A5), Route B, $^{31}$P-NMR $C_6D_6$: 87.8; 88.1 ppm, isomers;

$^iPr$(Ph)N—P(Ph)-N(Me)-P(Ph)-N(Ph)$^iPr$ (A6), Route B, $^{31}$P-NMR $C_6D_6$: 98.7; 100.2 ppm, isomers;

H(Ph)N—P(Ph)-N(Me)-P(Ph)-N(Ph)H (A7), Route A, $^{31}$P-NMR $C_6D_6$: 70.0; 73.3 ppm, isomers;

H($^iPr$)N—P(Ph)-N($^iPr$)—P(Ph)-N($^iPr$)H (A8); $^{31}$P-NMR $C_6D_6$: 60.6 ppm, major isomer isolated;

Et(Me)N—P(Ph)-N($C_6H_{11}$)—P(Ph)-N(Me)Et (A9), Route A, $^{31}$P-NMR $C_6D_6$: 93.4; 85.9 ppm, isomers;

Et(Me)N—P(Me)-N(Me)-P(Me)-N(Me)Et (A10), Route A, $^{31}$P-NMR $C_6D_6$: 84.0 ppm broad, isomers.

Example 2

Catalyst Preparation; General Procedure

Suitable amounts of the ligands and Cr(III)acetylacetonate as chromium precursor, at a ligand to Cr ratio of 1.25, were weighed in and charged to a Schlenk tube under inert atmosphere. A volume of 75 ml anhydrous solvent (see Table 1 for details) was added and the solution was stirred by means of a magnetic stirrer. After the Cr-compound and corresponding ligand dissolved, 5 ml of a solution of MMAO-3A (7 wt % Al in heptane (Akzo)) was added. The solution was immediately transferred to the reactor and the reaction was started. The reaction was stopped either when the maximum uptake of ethylene (80 g) was reached or after a predefined time by closing the ethylene inlet valve, cooling to room temperature, depressurizing and opening the reactor.

The liquid product mixture was quenched with diluted HCl and analyzed using gas chromatography with a known amount of dodecahydrotriphenylene internal standard. Any solid by-products, i.e., waxes, polyethylene, were filtered-off, dried, and weighed.

Standard reaction conditions are: $p_{ethylene}$=30 bar, T=60° C., co-catalyst=5 mL MMAO-3A (7 wt % Al in heptane), 75 mL solvent, $n_{Cr}$=0.034 mmol, [Ligand]/[Cr]=1.25 mol/mol.

Example 3

Oligomerization Process

A standard ethylene oligomerization reaction was carried out as follows:

Prior to conducting any experimenting, a 300 ml pressure reactor was heated to 100° C. at reduced pressure for several hours to eliminate traces of water, oxygen and oxygenated impurities.

The reactor, equipped with dip tube, thermowell, gas entrainment stirrer, cooling coil, control units for temperature, pressure and stirrer speed (all hooked up to a data acquisition system) was then inertized by sparging with dry argon. An isobaric ethylene supply was maintained by placing an aluminum, pressurized gas cylinder on a balance. Ethylene consumption was monitored via weight loss of the cylinder over time by means of a computerized data acquisition system.

Oligomerization Results

Table 1 summarizes the results of ethylene oligomerization experimental runs performed under these standard conditions and using catalyst systems prepared with the NPNPN-ligand structures (A1)-(A10). The Table shows the respective selectivities for C4, C6, C8, and C10+ olefin fractions in wt. % in the liquid phase. Numbers in parentheses denote wt.-percent of the respective linear alpha-olefin in the overall $C_6/C_8$ fraction. These LAO purities are generally advantageously high, while the ratio between 1-hexene and 1-octene is strongly determined by the groups $R^1$ to $R^7$ and can, thus, be varied to a considerable extent by the choice of substituents. Furthermore, a reasonably fine adjustment of the 1-C6/1-C8-LAO ratio can be achieved by variation of the solvent. The C10+-fraction is advantageously used as a reactor flushing medium for cleaning the equipment from side-product waxes and polyethylene.

The results show that LAO purities are generally advantageously high, while the ratio between 1-hexene and 1-octene varies depending on group $R^1$ to $R^7$. Thus, the ratio can be varied to a considerable extent by the choice of substituents. The ratio can also be adjusted to predetermined value by selecting group $R^1$ to $R^7$. Furthermore, reasonable fine-tuning of the 1-C6/1-C8-LAO ratio can be achieved by selecting the solvent. The C10+ fraction is advantageously used as a reactor flushing medium for cleaning the equipment from side-product waxes and polyethylene. Regarding the latter, the results show that the amount of solids formed is advantageously low.

The invention is further illustrated by the following embodiments.

Embodiment 1

A catalyst composition for the oligomerization of ethylene to produce 1-hexene or 1-octene, the catalyst composition comprising: a chromium compound; an NPNPN ligand of the formula $(R^1)(R^2)N—P(R^3)—N(R^4)—P(R^5)—N(R^6)(R^7)$, wherein $R^1$, $R^2$, $R^3$, $R^4$, $R^5$, $R^6$, and $R^7$ are each independently hydrogen, halogen, amino, trimethylsilyl or $C_1$-$C_{20}$ hydrocarbyl, preferably straight-chain or branched $C_1$-$C_{10}$ alkyl, phenyl, $C_6$-$C_{20}$ aryl or $C_6$-$C_{20}$ alkyl-substituted phenyl, optionally wherein the ligand is a cyclic derivative wherein at least one of the P or N atoms of the ligand is a member of a ring system, or any cyclic derivative thereof wherein at least one of the P or N atoms of the NPNPN ligand is a member of a ring system, the ring system being formed from one or more constituent compounds of the ligand by substitution; and an activator or co-catalyst.

Embodiment 2

The catalyst composition of embodiment 1, wherein the chromium compound comprises an organic salt, an inorganic salt, a coordination complex, or an organometallic complex of Cr(II) or Cr(III).

Embodiment 3

The catalyst composition of embodiment 1 or 2, wherein the chromium compound comprises Cr(III)acetylacetonate,

TABLE 1

Results of catalytic tests using NPNPN-ligands (A1) to (A10)

| Ligand No. (A_) | Solvent | time in min | g Products | g Solids | C4, wt % | C6 (1-C6), wt % | C8 (1-C8), wt % | C10+, wt % | Ratio (g 1-C6) to (g 1-C8)** |
|---|---|---|---|---|---|---|---|---|---|
| 1* | $C_6H_5Cl$ | 25 | 80 | 0.3 | 0.6 | 39.2 (94.9) | 37.5 (99.2) | 22.7 | 1.00 |
| 1 | toluene | 30 | 80 | 0.5 | 0.7 | 26.0 (90.3) | 56.3 (99) | 17.0 | 0.42 |
| 2 | $C_6H_5Cl$ | 35 | 80 | 1.0 | 1.0 | 41.2 (90.7) | 45.4 (99.3) | 12.4 | 0.86 |
| 2 | toluene | 15 | 80 | 0.8 | 0.8 | 42.1 (91.4) | 43.9 (99) | 13.2 | 0.88 |
| 3 | $C_6H_5Cl$ | 30 | 80 | 0.9 | 0.8 | 39.2 (91.5) | 46.6 (99.3) | 13.4 | 0.78 |
| 3 | toluene | 60 | 35 | 1.9 | 1.3 | 33.6 (89.6) | 57.1 (99.3) | 8.0 | 0.53 |
| 4 | $C_6H_5Cl$ | 35 | 80 | 9.0 | 0.6 | 67.0 (98.2) | 19.8 (99.4) | 12.6 | 3.34 |
| 4 | toluene | 30 | 80 | 8.0 | 0.4 | 65.6 (98.5) | 23.4 (99.4) | 10.6 | 2.78 |
| 5 | $C_6H_5Cl$ | 30 | 80 | 3.0 | 0.6 | 69.9 (98.4) | 11.7 (99.2) | 10.8 | 5.93 |
| 6 | $C_6H_5Cl$ | 20 | 80 | 3.7 | 1.8 | 58.5 (92.4) | 30.7 (99.3) | 9.0 | 1.77 |
| 7 | $C_6H_5Cl$ | 60 | 19 | 9.1 | 0.5 | 53.6 (84.9) | 28.2 (98.5) | 17.7 | 1.64 |
| 8 | $C_6H_5Cl$ | 60 | 25 | 2.7 | 1.4 | 61.1 (97) | 24.9 (99) | 12.6 | 2.40 |
| 9 | $C_6H_5Cl$ | 45 | 80 | 2.5 | 0.8 | 46.8 (97.1) | 38.5 (99) | 13.9 | 1.19 |
| 9 | toluene | 50 | 80 | 0.4 | 0.8 | 39.5 (98.1) | 44.4 (99.3) | 15.3 | 0.88 |
| 10 | $C_6H_5Cl$ | 60 | 50 | 1.9 | 1.6 | 47.2 (93.9) | 43.0 (99.1) | 8.2 | 1.04 |

*20 bar
Ratio (g 1-C6) to (g 1-C8) = (C6*(1-C6)/100)/(C8*(1-C8)/100))

Cr(III)octanoate, CrCl$_3$(tetrahydrofuran)$_3$, Cr(III)-2-ethylhexanoate, chromium hexacarbonyl, Cr(III)chloride, benzene(tricarbonyl)-chromium or a combination comprising at least one of the foregoing.

Embodiment 4

The catalyst composition of any one or more of embodiments 1 to 3, wherein R$^1$, R$^2$, R$^3$, R$^4$, R$^5$, R$^6$ and R$^7$ are each independently hydrogen, methyl (Me), ethyl (Et), isopropyl ($^i$Pr), tert-butyl ($^t$Bu), n-hexyl, phenyl (Ph).

Embodiment 5

The catalyst composition of any one or more of embodiments 1 to 4, wherein the activator or co-catalyst comprises trimethylaluminum, triethylaluminum, tri-isopropylaluminum, tri-isobutylaluminum, diethylaluminum chloride, ethylaluminum sesquichloride, ethylaluminum dichloride, methylaluminoxane, preferably modified methylaluminoxane, more preferably MMAO-3A, or a combination comprising at least one of the foregoing.

Embodiment 6

The catalyst composition of any one or more of embodiments 1 to 5, wherein the ligand comprises Et(Me)N—P(Ph)-N(Me)-P(Ph)-N(Me)Et, C$_6$H$_{11}$(Me)N—P(Ph)-N(Me)-P(Ph)-N(Me)C$_6$H$_{11}$, $^i$Pr(Me)N—P(Ph)-N(Me)-P(Ph)-N(Me)$^i$Pr, H($^t$Bu)N—P(Ph)-N(Me)-P(Ph)-N($^t$Bu)H, (C$_6$H$_{11}$)$_2$N—P(Ph)-N(Me)-P(Ph)-N(C$_6$H$_{11}$)$_2$, $^i$Pr(Ph)N—P(Ph)-N(Me)-P(Ph)-N(Ph)$^i$Pr, H(Ph)N—P(Ph)-N(Me)-P(Ph)-N(Ph)H, H($^i$Pr)N—P(Ph)-N($^i$Pr)—P(Ph)-N($^i$Pr)H, Et(Me)N—P(Ph)-N(C$_6$H$_{11}$)—P(Ph)-N(Me)Et, Et(Me)N—P(Me)-N(Me)-P(Me)-N(Me)Et, or a combination comprising at least one of the foregoing.

Embodiment 7

The catalyst composition of any one or more of embodiments 1 to 6, further comprising a solvent, preferably wherein the solvent is toluene, chlorobenzene, o-dichlorobenzene, bromobenzene, chlorocyclohexane, chlorohexane, multiple halogenated aromatic mixtures, or a combination comprising at least one of the foregoing.

Embodiment 8

The catalyst composition of any one or more of embodiments 1 to 7, wherein the concentration of the chromium compound is from about 0.01 to about 10 mmol/l, preferably about 0.1 to about 1.0 mmol/l.

Embodiment 9

The catalyst composition of any one or more of embodiments 1 to 8, wherein the molar ligand/Cr ratio is from about 1.0 to about 5.0, preferably about 1.0 to about 1.5.

Embodiment 10

The catalyst composition of any one or more of embodiments 1 to 9, wherein the molar Al/Cr-ratio is from about 1 to about 500, preferably about 50 to about 300.

Embodiment 11

The catalyst composition of any one or more of embodiments 1 to 10, wherein the chromium compound is Cr(III) acetylacetonate, the NPNPN ligand is Et(Me)N—P(Ph)-N(Me)-P(Ph)-N(Me)Et; and the activator or co-catalyst is MMAO-3A.

Embodiment 12

A process for the oligomerization of ethylene, comprising contacting ethylene with the catalyst composition of any one of embodiments 1 to 11 under ethylene oligomerization conditions effective to produce 1-hexene or 1-octene.

Embodiment 13

The process of embodiment 12, wherein the contacting is at a pressure of from about 10 to about 100 bar, preferably about 20 to about 70 bar.

Embodiment 14

The process of embodiment 12 or 13, wherein the contacting is at a temperature of from about 30° C. to about 100° C., preferably about 40° C. to about 70° C.

Embodiment 15

The process of any one or more of embodiments 12 to 14, wherein the mean residence time is from 10 minutes to about 20 hours.

Embodiment 16

The process of any one or more of embodiments 12 to 15, wherein a weight ratio of 1-hexene to 1-octene is in the range from about 0.1 to 10, preferably about 0.2 to 8.

Embodiment 17

A catalyst composition, obtained by combining at least: a chromium compound; an NPNPN ligand of the formula (R$^1$)(R$^2$)N—P(R$^3$)—N(R$^4$)—P(R$^5$)—N(R$^6$)(R$^7$), wherein R$^1$, R$^2$, R$^3$, R$^4$, R$^5$, R$^6$, and R$^7$ are each independently hydrogen, halogen, amino, trimethylsilyl or C$_1$-C$_{20}$ hydrocarbyl, preferably straight-chain or branched C$_1$-C$_{10}$ alkyl, phenyl, C$_6$-C$_{20}$ aryl or C$_6$-C$_{20}$ alkyl-substituted phenyl, optionally wherein the ligand is a cyclic derivative wherein at least one of the P or N atoms of the ligand is a member of a ring system, or any cyclic derivative thereof wherein at least one of the P or N atoms of the NPNPN ligand is a member of a ring system, the ring system being formed from one or more constituent compounds of the ligand by substitution; and an activator or co-catalyst.

Embodiment 18

An ethylene oligomerization reaction producing 1-hexene and 1-octene, wherein the selectivity for 1-hexene or 1-octene is at least about 90%.

Embodiment 19

The ethylene oligomerization reaction of claim 18 comprising a chromium-based catalytic system.

Embodiment 20

The ethylene oligomerization reaction of embodiment 19, wherein the chromium-based catalytic system comprises:
a chromium compound;
an NPNPN ligand of the formula $(R^1)(R^2)N—P(R^3)—N(R^4)—P(R^5)—N(R^6)(R^7)$ wherein $R^1$, $R^2$, $R^3$, $R^4$, $R^5$, $R^6$, and $R^7$ are each independently hydrogen, halogen, amino, trimethylsilyl, $C_1$-$C_{20}$ hydrocarbyl, preferably straight-chain or branched $C_1$-$C_{10}$ alkyl, phenyl, $C_6$-$C_{20}$ aryl, $C_6$-$C_{20}$ alkyl-substituted phenyl, optionally wherein the ligand is a cyclic derivative wherein at least one of the P or N atoms of the ligand is a member of a ring system, or any cyclic derivative thereof wherein at least one of the P or N atoms of the NPNPN ligand is a member of a ring system, the ring system being formed from one or more constituent compounds of the ligand by substitution; and an activator or co-catalyst.

Embodiment 21

A linear alpha olefin composition resulting from an ethylene oligomerization process, wherein ratio by weight of 1-hexene to 1-octene is at least about about 0.2 to about 8.

Embodiment 22

The linear alpha olefin composition of embodiment 21, wherein the ratio by weight of 1-hexene to 1-octene is at least about 1.64 to about 5.93.

Embodiment 23

The linear alpha olefin composition of embodiment 22, wherein the ratio by weight of 1-hexene to 1-octene is at least about 5.93.

The singular forms "a," "an," and "the" include plural referents unless the context clearly dictates otherwise. "Or" means "and/or."

The endpoints of all ranges directed to the same component or property are inclusive and independently combinable (e.g., ranges of "less than or equal to about 25 wt %, or 5 wt % to about 20 wt %," is inclusive of the endpoints and all intermediate values of the ranges of "5 wt % to about 25 wt %," etc.). Disclosure of a narrower range or more specific group in addition to a broader range is not a disclaimer of the broader range or larger group.

Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

What is claimed is:

1. A catalyst composition for the oligomerization of ethylene to produce 1-hexene or 1-octene, the catalyst composition comprising:
a chromium compound;
an NPNPN ligand of the formula $(R^1)(R^2)N—P(R^3)—N(R^4)—P(R^5)—N(R^6)(R^7)$ wherein $R^2$, $R^3$, $R^4$, $R^5$, $R^6$, and $R^7$ are each independently hydrogen, halogen, amino, trimethylsilyl, $C_1$-$C_{20}$ hydrocarbyl, phenyl, $C_6$-$C_{20}$ aryl, or $C_6$-$C_{20}$ alkyl-substituted phenyl; and
an activator or co-catalyst.

2. The catalyst composition of claim 1, wherein the chromium compound comprises an organic salt, an inorganic salt, a coordination complex, or an organometallic complex of Cr(0) or Cr(III).

3. The catalyst composition of claim 1, wherein the chromium compound comprises Cr(III)acetylacetonate, Cr(III)octanoate, CrCl$_3$(tetrahydrofuran)$_3$, Cr(III)-2-ethylhexanoate, chromium hexacarbonyl, Cr(III)chloride, benzene(tricarbonyl)-chromium, or a combination comprising at least one of the foregoing.

4. The catalyst composition of claim 1, wherein $R^1$, $R^2$, $R^3$, $R^4$, $R^5$, $R^6$, and $R^7$ are each independently hydrogen, chloro, methyl, ethyl, isopropyl, tert-butyl, n-hexyl, or phenyl.

5. The catalyst composition of claim 1, wherein the activator or co-catalyst comprises trimethylaluminum, triethylaluminum, tri-isopropylaluminum, tri-isobutylaluminum, diethylaluminum chloride, ethylaluminum sesquichloride, ethylaluminum dichloride, methylaluminoxane, or a combination comprising at least one of the foregoing.

6. The catalyst composition of claim 1, wherein the ligand comprises
Et(Me)N—P(Ph)-N(Me)-P(Ph)-N(Me)Et,
C$_6$H$_{11}$(Me)N—P(Ph)-N(Me)-P(Ph)-N(Me)C$_6$H$_{11}$,
$^i$Pr(Me)N—P(Ph)-N(Me)-P(Ph)-N(Me)$^i$Pr,
H($^t$Bu)N—P(Ph)-N(Me)-P(Ph)-N($^t$Bu)H,
(C$_6$H$_{11}$)$_2$N—P(Ph)-N(Me)-P(Ph)-N(C$_6$H$_{11}$)$_2$,
$^i$Pr(Ph)N—P(Ph)-N(Me)-P(Ph)-N(Ph)$^i$Pr,
H(Ph)N—P(Ph)-N(Me)-P(Ph)-N(Ph)H,
H($^i$Pr)N—P(Ph)-N($^i$Pr)—P(Ph)-N($^i$Pr)H,
Et(Me)N—P(Ph)-N(C$_6$H$_{11}$)—P(Ph)-N(Me)Et,
Et(Me)N—P(Me)-N(Me)-P(Me)-N(Me)Et,
or a combination comprising at least one of the foregoing.

7. The catalyst composition of claim 1, further comprising a solvent.

8. The catalyst composition of claim 7, wherein the solvent is toluene, chlorobenzene, o-dichlorobenzene, bromobenzene, chlorocyclohexane, chlorohexane, multiple halogenated aromatic mixtures, or a combination comprising at least one of the foregoing.

9. The catalyst composition of claim 1, wherein the concentration of the chromium compound is from about 0.01 to about 10 mmol/l.

10. The catalyst composition of claim 1, wherein the molar ligand/Cr ratio is from about 1.0 to about 5.0.

11. The catalyst composition of claim 1, wherein the molar Al/Cr ratio is from about 1 to about 500.

12. The catalyst composition of claim 1, wherein the $C_1$-$C_{20}$ hydrocarbyl is straight-chain or branched $C_1$-$C_{10}$ alkyl.

13. The catalyst composition of claim 1, wherein the activator or co-catalyst comprises modified methylaluminoxane.

14. A catalyst composition for the oligomerization of ethylene to produce 1-hexene or 1-octene, the catalyst composition comprising:
Cr(III)acetylacetonate,
Et(Me)N—P(Ph)-N(Me)-P(Ph)-N(Me)Et; and
MMAO-3A.

15. A process for the oligomerization of ethylene, comprising
contacting ethylene with the catalyst composition of claim 1 under ethylene oligomerization conditions effective to produce 1-hexene or 1-octene.

16. The process of claim 15, wherein the contacting is at a pressure of from 10 to 100 bar.

17. The process of claim 15, wherein the contacting is at a temperature of from 30° C. to 100° C.

18. The process of claim 15, wherein the mean residence time is from 10 minutes to 20 hours.

19. The process of claim 15, wherein a weight ratio of 1-hexene to 1-octene is in the range from 0.1 to 10.

20. An ethylene oligomerization reaction producing 1-hexene and 1-octene, wherein the selectivity for 1-hexene or 1-octene is at least 90%, comprising a chromium-based catalytic system, wherein the chromium-based system comprises: a chromium compound; an NPNPN ligand of the formula $(R^1)(R^2)N—P(R^3)—N(R^4)—P(R^5)—N(R^6)(R^7)$ wherein $R^1$, $R^2$, $R^3$, $R^4$, $R^5$, $R^6$ and $R^7$ are each independently hydrogen, halogen, amino, trimethylsilyl, $C_1$-$C_{20}$ hydrocarbyl, phenyl, $C_6$-$C_{20}$ aryl, $C_6$-$C_{20}$ alkyl-substituted phenyl, optionally wherein the ligand is a cyclic derivative wherein at least one of the P or N atoms of the ligand is a member of a ring system, or any cyclic derivative thereof wherein at least one of the P or N atoms of the NPNPN ligand is a member of a ring system, the ring system being formed from one or more constituent compounds of the ligand by substitution; and an activator or co-catalyst.

\* \* \* \* \*